US012714813B2

(12) United States Patent
Wiemker et al.

(10) Patent No.: US 12,714,813 B2
(45) Date of Patent: Aug. 25, 2026

(54) PATIENT STRATIFICATION AND CLINICAL DECISION SUPPORT ON MECHANICAL VENTILATION SETTINGS FROM SONAR RESPONSES THROUGH AN ENDOTRACHEAL TUBE (ETT)

(71) Applicant: KONINKLIJKE PHILIPS N.V., Eindhoven (NL)

(72) Inventors: Rafael Wiemker, Hamburg (DE); Joerg Sabczynski, Hamburg (DE); Thomas Koehler, Hamburg (DE); Cornelis Petrus Hendriks, Eindhoven (NL); Roberto Buizza, Eindhoven (NL); Jaap Roger Haartsen, Eindhoven (NL); Stefan Winter, Aachen (DE); Michael Polkey, London (GB); Rita Priori, Eindhoven (NL); Nataly Wieberneit, Hamburg (DE); Kiran Hamilton J. Dellimore, Eindhoven (NL)

(73) Assignee: Koninklijke Philips N.V., Eindhoven (NL)

(*) Notice: Subject to any disclaimer, the term of this patent is extended or adjusted under 35 U.S.C. 154(b) by 995 days.

(21) Appl. No.: 17/960,167

(22) Filed: Oct. 5, 2022

(65) Prior Publication Data

US 2023/0133142 A1 May 4, 2023

Related U.S. Application Data

(60) Provisional application No. 63/274,560, filed on Nov. 2, 2021.

(51) Int. Cl.
*A61M 16/00* (2006.01)
*A61B 8/00* (2006.01)
(Continued)

(52) U.S. Cl.
CPC ............. *A61M 16/026* (2017.08); *A61B 8/12* (2013.01); *A61B 8/5207* (2013.01); *A61M 16/04* (2013.01);
(Continued)

(58) Field of Classification Search
CPC ................ A61M 16/04; A61M 16/026; A61M 2205/3375; A61M 2230/40; A61B 5/7282;
(Continued)

(56) References Cited

U.S. PATENT DOCUMENTS 6,705,319 B1 3/2004 Wodicka
11,696,993 B2 * 7/2023 Mansfield ......... A61M 16/0051 128/207.14

(Continued)

FOREIGN PATENT DOCUMENTS

WO 2013149138 A1 10/2013

OTHER PUBLICATIONS

Dubois, A.B. et al., "Oscillation mechanics of lungs and chest in man." J ApplPhysiol 1956.

(Continued)

*Primary Examiner* — Douglas Y Sul
(74) *Attorney, Agent, or Firm* — Daniel H. Brean

(57) ABSTRACT

A respiration monitoring device comprises an electronic controller configured to: receive an audio signal that is acoustically coupled with an airway of a patient receiving mechanical ventilation therapy from a mechanical ventilator; map the audio signal to one or more lung disease or injury condition categories; and at least one of: display the mapped one or more lung disease or injury condition categories on a display device; and determine a recommended adjustment to one or more parameters of the mechanical ventilation therapy delivered to the patient based at least on (Continued)

the mapped lung disease or injury condition categories and displaying the recommended adjustment on the display device.

11 Claims, 3 Drawing Sheets

(51) Int. Cl.
*A61B 8/12* (2006.01)
*A61M 16/04* (2006.01)
*G16H 20/40* (2018.01)
*G16H 30/40* (2018.01)
*G16H 50/70* (2018.01)

(52) U.S. Cl.
CPC ............. *G16H 20/40* (2018.01); *G16H 30/40* (2018.01); *G16H 50/70* (2018.01); *A61M 2205/3375* (2013.01); *A61M 2230/40* (2013.01)

(58) Field of Classification Search
CPC ... A61B 5/7275; A61B 5/7267; A61B 5/0803; A61B 5/08
See application file for complete search history.

(56) References Cited

U.S. PATENT DOCUMENTS

2002/0183642 A1* 12/2002 Murphy ................ A61B 5/061 600/529
2003/0018276 A1 1/2003 Mansy
2003/0034035 A1 2/2003 Raphael
2006/0037615 A1* 2/2006 Wilkinson ............ A61B 5/085 128/204.23
2011/0265795 A1 11/2011 Tagawa
2012/0116156 A1 5/2012 Lederman
2021/0121651 A1 4/2021 Schaner
2021/0316094 A1* 10/2021 Kimm ................. A61B 8/5207
2023/0148954 A1* 5/2023 Lyon ..................... G16H 20/40 600/529
2024/0001061 A1* 1/2024 Barjaktarevic ....... A61M 39/10
2024/0207555 A1* 6/2024 Horzewski ............ G16H 50/70

OTHER PUBLICATIONS

Lo, P. et al., "Extraction of Airways from CT (EXACT09)", IEEE Transactions on Medical Imaging, vol. 31, No. 11, Nov. 2012.
Mai, N.T. et al., "Acoustic Image Simulator Based on Active Sonar Model in Underwater Environment", 2018 15th International Conference on Ubiquitous Robots (UR), 2018.
Wang, J.-Y, et al., "Dynamic Properties of Human Bronchial Airway Tissues," 2011, http://arxiv.org/abs/1111.5645.
Andrikakou, P. et al., "On the behaviour of lung tissue under tension and compression". Nature, Sci Rep 6, 3662 (2016), https://doi.org/10.1038/srep36642.
https://phyphox.org/wiki/index.php?title=Experiment:_ Sonar.
Choy, G. et al. "Current Applications and Future Impact of Machine Learning in Radiology." Radiology. 2018;288(2).
Rao, A. et al., "Acoustic Methods for Pulmonary Diagnosis." IEEE Rev Biomed Eng. 2019;12:221-239.
International Search Report for PCT/EP2022/080052 filed Oct. 27, 2022.
Aliboni, L. et al., "Simulation of bronchial airway acoustics in healthy and asthmatic subjects". PLOS One, vol. 15, No. 2 (2020), p. e0228603.
Farhat, H. et al., "Deep learning applications in pulmonary medical imaging: recent updates and insights on COVID-19". Machine Vision adn Applications, Springer Verlag, DE, vol. 31, No. 6 (2020), XP037204544.

* cited by examiner

PATIENT STRATIFICATION AND CLINICAL DECISION SUPPORT ON MECHANICAL VENTILATION SETTINGS FROM SONAR RESPONSES THROUGH AN ENDOTRACHEAL TUBE (ETT)

CROSS-REFERENCE TO RELATED APPLICATIONS

This patent application claims the priority benefit under 35 U.S.C. § 119(e) of U.S. Provisional Application No. 63/274,560, filed on Nov. 2, 2021, the contents of which are herein incorporated by reference.

The following relates generally to the respiratory therapy arts, mechanical ventilation arts, respiratory monitoring arts, clinical decision arts, and related arts.

BACKGROUND

Mechanical ventilation (MV) of a patient typically entails placement of an endotracheal tube (ETT) into a trachea of the patient, in a process known as tracheal intubation. The desired position of the tip of an ETT is approximately 5.0 cm (±2.0 cm) above a carina (i.e., the location where the trachea splits into the main right and left bronchus). Tracheal intubation is usually performed by an anesthesiologist or other qualified medical professional, and in a common sequence the head is moved backward to access the airway, and a laryngoscope is used to facilitate proper placement of the ETT between the vocal cords and into the trachea, without misplacement into the esophagus.

Common situations where mechanical ventilation is required can include intensive care unit (ICU) cases and during major surgery. Such patients often have images (e.g., computed tomography (CT) images) obtained of the thorax before being sent to the ICU, in particular if the patient's condition is a lung-related disease (e.g., Covid-19), or trauma.

Mechanical ventilation settings of a mechanical ventilator must be adjusted specifically to a patient and a disease/injury of the patient. In particular, volume or pressure limits have to be chosen in order to limit the likelihood of ventilation induced injuries on the one hand, but yield effective oxygenation on the other hand. Determination of a lung anatomy of the patient and/or a disease/injury status of the patient can be done via imaging (e.g., X-ray or computed tomography (CT) imaging). However, in many situations, such imaging equipment is unavailable, or it may be difficult and time consuming to schedule an imaging session, and providing continuous respiratory monitoring by way of medical imaging is expensive and often impractical.

The following discloses certain improvements to overcome these problems and others.

SUMMARY

In one aspect, a respiration monitoring device comprises an electronic controller configured to: receive an audio signal that is acoustically coupled with an airway of a patient receiving mechanical ventilation therapy from a mechanical ventilator; map the audio signal to one or more lung disease or injury condition categories; and at least one of: display the mapped one or more lung disease or injury condition categories on a display device; and determine a recommended adjustment to one or more parameters of the mechanical ventilation therapy delivered to the patient based at least on the mapped lung disease or injury condition categories and displaying the recommended adjustment on the display device.

In another aspect, a respiration monitoring method comprises, with an electronic controller: receiving an audio signal that is acoustically coupled with an airway of a patient receiving mechanical ventilation therapy from a mechanical ventilator; mapping the audio signal to one or more lung disease or injury condition categories; and at least one of: displaying the mapped one or more lung disease or injury condition categories on a display device; and determining a recommended adjustment to one or more parameters of the mechanical ventilation therapy delivered to the patient based at least on the mapped lung disease or injury condition categories and displaying the recommended adjustment on the display device.

One advantage resides in detecting a status of lungs of a patient without the use of a conventional imaging device.

Another advantage resides in detecting a status of lungs of a patient without irradiating the patient.

Another advantage resides in detecting a status of lungs of a patient without using expensive sensors and leveraging an ETT used to ventilate the patient.

Another advantage resides in detecting a status of lungs of a patient using a sonar response and outputting the sonar response on a consumer mobile device (e.g., a smartphone, a tablet, etc.).

Another advantage resides in detecting a status of lungs of a patient using sonar data analyzed by a low cost, trained machine learning model.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
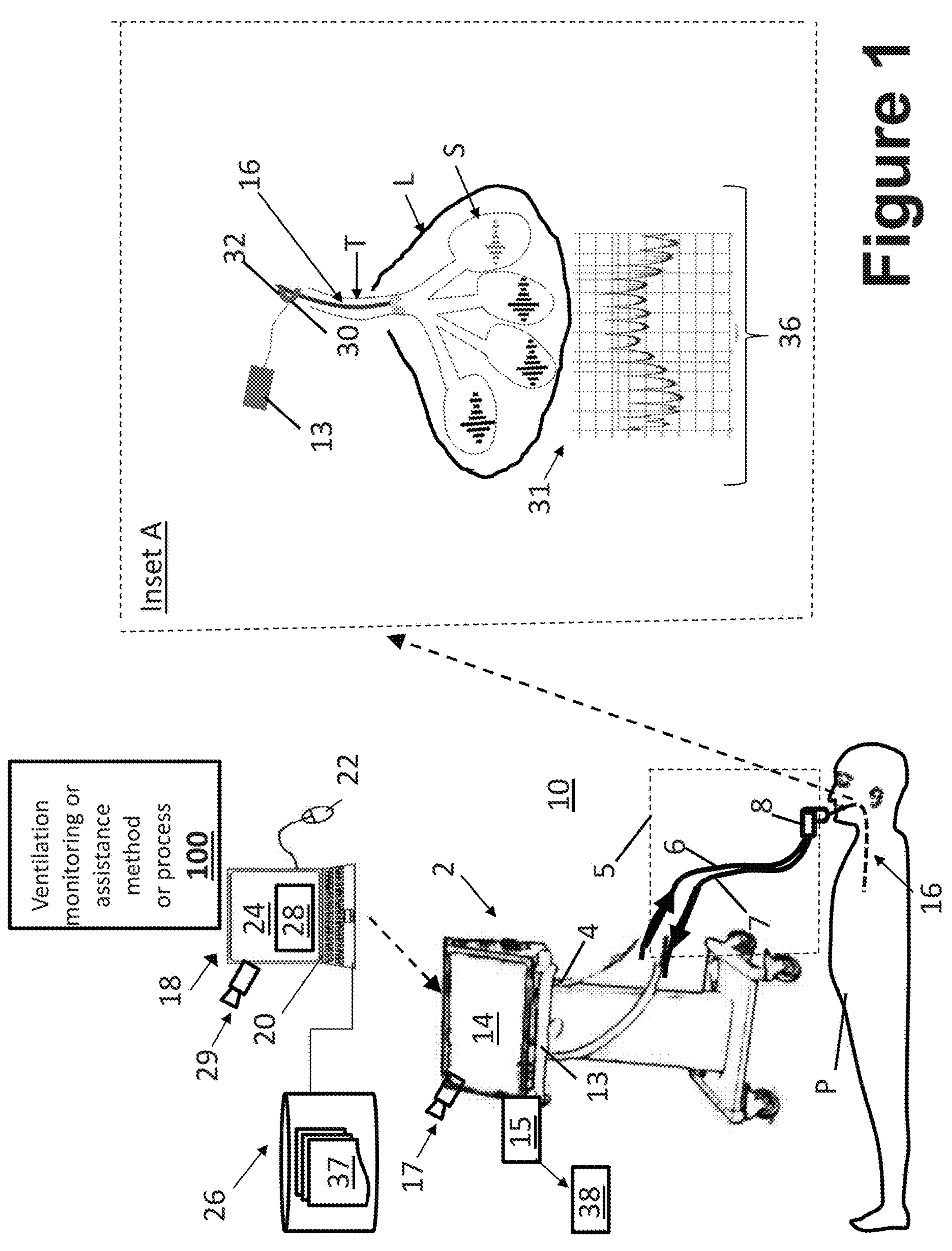
FIG. 1 diagrammatically shows an illustrative mechanical ventilation system in accordance with the present disclosure.

As used herein, the singular form of "a", "an", and "the" include plural references unless the context clearly dictates otherwise. As used herein, statements that two or more parts or components are "coupled," "connected," or "engaged" shall mean that the parts are joined, operate, or co-act together either directly or indirectly, i.e., through one or more intermediate parts or components, so long as a link occurs. Directional phrases used herein, such as, for example and without limitation, top, bottom, left, right, upper, lower, front, back, and derivatives thereof, relate to the orientation of the elements shown in the drawings and are not limiting upon the scope of the claimed invention unless expressly recited therein. The word "comprising" or "including" does not exclude the presence of elements or steps other than those described herein and/or listed in a claim. In a device comprised of several means, several of these means may be embodied by one and the same item of hardware.

With reference to FIG. 1, a mechanical ventilator 2 for providing ventilation therapy to an associated patient P is shown. As shown in FIG. 1, the mechanical ventilator 2 includes an outlet 4 connectable with a patient breathing circuit 5 to delivery mechanical ventilation to the patient P. The patient breathing circuit 5 includes typical components for a mechanical ventilator, such as an inlet line 6, an optional outlet line 7 (this may be omitted if the ventilator employs a single-limb patient circuit), a connector or port 8 for connecting with an ETT, and one or more breathing sensors (not shown), such as a gas flow meter, a pressure sensor, end-tidal carbon dioxide ($etCO_2$) sensor, and/or so forth. The mechanical ventilator 2 is designed to deliver air, an air-oxygen mixture, or other breathable gas (supply not shown) to the outlet 4 at a programmed pressure and/or flow rate to ventilate the patient via an ETT. The mechanical ventilator 2 also includes a controller 13 (e.g., an electronic processor or a microprocessor), a display device 14 (e.g., an LCD display, plasma display, cathode ray tube display, and/or so forth)., and a non-transitory computer readable medium 15 storing instructions executable by the controller 13. The non-transitory computer readable medium 15 may, by way of non-limiting illustrative example, include one or more of a magnetic disk, RAID, or other magnetic storage medium; a solid-state drive, flash drive, electronically erasable read-only memory (EEROM) or other electronic memory; an optical disk or other optical storage; various combinations thereof; or so forth; and may be for example a network storage, an internal hard drive, various combinations thereof, or so forth.

FIG. 1 diagrammatically illustrates the patient P intubated with an endotracheal tube (ETT) 16 (the lower portion of which is inside the patient P and hence is shown in phantom). The connector or port 8 connects with the ETT 16 to operatively connect the mechanical ventilator 2 to deliver breathable air to the patient P via the ETT 16. The mechanical ventilation provided by the mechanical ventilator 2 via the ETT 16 may be therapeutic for a wide range of conditions, such as various types of pulmonary conditions like emphysema or pneumonia, viral or bacterial infections impacting respiration such as a COVID-19 infection or severe influenza, cardiovascular conditions in which the patient P receives breathable gas enriched with oxygen, or so forth.

FIG. 1 shows the patient P already intubated. That is, FIG. 1 shows the patient after a tracheal intubation has been performed to insert the ETT 16 into the patient. However, to safely perform the tracheal intubation, the anesthesiologist or other qualified medical professional first performs an assessment of the patient P to select the ETT size of the ETT 16, and then inserts an ETT of the selected size into the patient P by a tracheal intubation procedure.

With continuing reference to FIG. 1, a respiration monitoring device 18 can be included, and configured to assist with detecting a presence of a lung disease or injury condition in the patient P and, in some embodiments, to provide recommended adjustment(s) to the mechanical ventilation therapy. The respiration monitoring device 18 can comprise an electronic processing device, such as a workstation computer (more generally, a computer), a smart device (e.g., a smartphone, a tablet, and so forth), or server computer or a plurality of server computers, (e.g., interconnected to form a server cluster, cloud computing resource, or so forth). In some embodiments, the respiratory monitoring device 18 may be integral with the controller 13 of the mechanical ventilator 2, for example comprising additional programming of the controller 13. In some embodiments, the respiratory monitoring device may be integral with a multifunction bedside patient monitor, for example comprising additional programming of the patient monitor. The respiration monitoring device 18 includes typical components, such as an electronic controller 20 (e.g., an electronic processor or a microprocessor), optionally at least one user input device (e.g., a mouse, a keyboard, a trackball, a finger swipe on a touchscreen of a smart device, and/or the like) 22, and at least one display device 24 (e.g., an LCD display, plasma display, cathode ray tube display, and/or so forth) and/or other output device. In some embodiments, the display device 24 can be a separate component from the electronic processing device 18. The display device 24 may also comprise two or more display devices.

The electronic controller 20 is operatively connected with a one or more non-transitory storage media 26. The non-transitory storage media 26 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the respiratory assistance device 18, various combinations thereof, or so forth. It is to be understood that any reference to a non-transitory medium or media 26 herein is to be broadly construed as encompassing a single medium or multiple media of the same or different types. Likewise, the electronic controller 20 may be embodied as a single electronic processor or as two or more electronic processors. The non-transitory storage media 26 stores instructions executable by the at least one electronic controller 20. The instructions include instructions to generate a graphical user interface (GUI) 28 for display on the remote operator display device 24. The electronic processing device 18 also includes a loudspeaker 29 for outputting audio signals.

As shown in inset A of FIG. 1, an acoustic coupler or audio transducer 30 is attached to a portion of the ETT 16 that is not disposed in the trachea of the patient P. The audio transducer 30 is configured to generate an audio signal 31 acoustically coupled with the ETT 16 of the patient P receiving MV therapy from the mechanical ventilator 2. In some examples, the intubation assistance device 18 can generate the audio signal 31. In other examples, the audio transducer 30 comprises a speaker 30. In addition, a microphone 32 is also acoustically coupled with the ETT 16 and configured to receive the audio signal 31. For example, the speaker 30 and the microphone 32 may be integrated into a click-on fastener that can be clipped on to the ETT 16, and in electronic communication (e.g., by a wired connection, or by a wireless connection such as a Bluetooth™ connection) with the electronic controller 13 of the mechanical ventilator 2 and/or the electronic controller 20 of the electronic processing device 18. (Note, Inset A diagrammatically indicates the electronic controller 13). The audio signal 31 acoustically couples with the trachea T and alveolar ducts and sacs S inside the lungs L (one lung L being shown in Inset A for illustration), and different acoustic resonances are observed for different lung disease or injury conditions. Inset A also shows the audio signal 31, and schematically shows resonant frequencies 36 within different portions of the lung of the patient P. In some examples, the microphone 32 can be located at an end of the ETT 16 that is inserted into the trachea of the patient P. Alternatively, instead of a speaker 30/microphone 32 combination, a forced oscillation technique (FOT) device can be used (see, e.g., Dubois A B, Brody A W, Lewis D H, et al., Oscillation mechanics of lungs and chest in man. J ApplPhysiol 1956).

In the illustrative example, the audio signal 31 is acoustically coupled with the airway T, L, S of the patient P receiving the mechanical ventilation therapy from the mechanical ventilator 2 by way of the ETT 16. More generally, however, the audio signal may be acoustically coupled with the airway via some other patient interface. For example, if the patient has undergone a tracheotomy to insert a breathing tube (not shown) directly into the trachea T, then the speaker 30 and microphone 32 could be coupled to that breathing tube.

Furthermore, as disclosed herein, the non-transitory computer readable medium 15 of the mechanical ventilator 2 and/or the non-transitory storage media 26 of the electronic processing device 18 stores instructions executable by the at least one electronic controller 13 of the mechanical ventilator 2, or the at least one electronic controller 20 of the electronic processing device 18 to perform a ventilation monitoring or assistance method or process 100.

Figure 2:
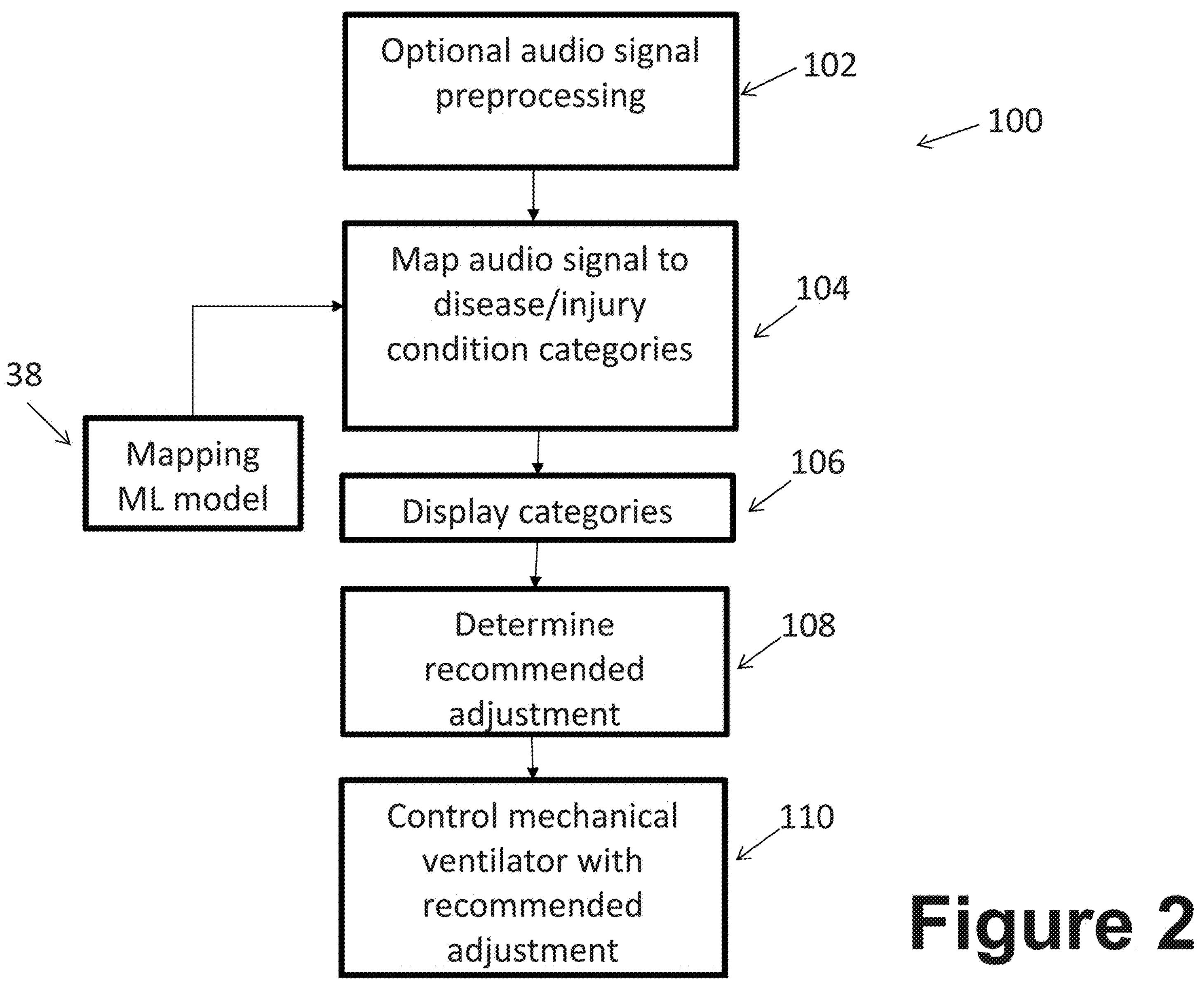
FIG. 2 shows an example flow chart of operations suitably performed by the system of FIG. 1.

With reference to FIG. 2, and with continuing reference to FIG. 1, an illustrative embodiment of the ventilation monitoring or assistance method 100 is diagrammatically shown as a flowchart. As described herein, the method 100 is performed by the electronic controller 13 of the mechanical ventilator 2. However, the method 100 can suitably be performed by the electronic controller 20 of the electronic processing device 18. For example, if a visual message generated during the method 100 can be displayed on the display device 14 of the mechanical ventilator 2, then the same message can be suitably displayed on the display device 24 of the electronic processing device 18. These are merely examples.

To begin the method 100, the ETT 16 can be inserted into the trachea of the patient P, and the speaker 30 and the microphone 32 can be clipped or otherwise attached to the portion of the ETT 16 (or integrated with the ETT 16) that is not inserted into the trachea of the patient P. At an operation 102, the audio signal 31 may optionally be pre-processed. For example, the raw audio signal 31 is a time-domain sound intensity-versus-time signal, and this could be processed in the operation 102 by a Fast Fourier Transform (FFT) to transform to a frequency domain representation which then serves as the input for subsequent analysis steps. In another example of pre-processing, the audio signal 31 is analyzed to extract resonant frequencies 36 of the airway of the patient P which then serve as the input for the subsequent analysis steps. The resonant frequencies extraction can be done using an FFT, although other approaches could be used, e.g., if the microphone generates a chirp signal in which the frequency ramps up or down with time then the resonant frequencies may be extracted directly from the time-domain signal. These are merely illustrative examples. In some embodiments, the pre-processing operation 102 is omitted and the raw time-domain audio signal serves as the input for subsequent analysis steps. As previously noted, the audio signal 31 is acoustically coupled with the ETT 16. The audio signal 31 can be, for example, a chirp signal, and the resonant frequencies 36, for example, can be in a range of 1 Hz-10 kHz, and in particular in a range of 100 Hz-5 kHz.

At an operation 104, (optionally preprocessed) audio signal 31 is mapped to one or more lung disease or injury condition categories (e.g., collapsed lobes, aeration states, infections, inflammations, effusions, ARRD, mucus build-up, airway constriction/collapsing, aeration deterioration, asthmatic exacerbation, effusion build-up, architectural airway remodeling, etc.). In some embodiments, the mapping operation 104 includes inputting the raw time-domain audio signal or the extracted resonant frequencies 36 or other preprocessed audio signal 31 representation to an audio signal-to-lung disease or injury condition mapping machine-learning (ML) model 38 (see also FIG. 1). For example, the model 38 can comprise a trained artificial neural network (ANN) 38 into the electronic controller 13 of the mechanical ventilator 2 (or the electronic controller 20 of the electronic processing device 18) to perform the mapping operation 104.

To train the ML model 38, training images 37 (see, FIG. 1, e.g., CT images obtained with a CT imaging device, which is not shown in FIG. 1 or 2) of a plurality of historical patients are obtained (e.g., from a database such as the non-transitory computer readable medium 26 of the electronic processing device 18). In another embodiment, the training images 37 can be generated by receiving as-acquired training images of the plurality of historical patients (e.g., from a database such as the non-transitory computer readable medium 26 of the electronic processing device 18). The as-acquired training images are segmented to delineate respiratory features including at least the lungs of the patients in the as-acquired training images. The delineated respiratory features can be modified in accordance with specific lung disease or injury categories to generate the training images 37. To segment the as-acquired training images, the airways are segmented in a three-dimensional representation (see, e.g., P. Lo, B. van Ginneken, J. M. Reinhardt, et al, Extraction of Airways from CT (EXACT09)", in IEEE TMI 2012). Based on this airway geometry, an acoustic simulation is performed (see, e.g., N. T. Mai, Y. Ji, H. Woo, Y. Tamura, A. Yamashita and H. Asama, Acoustic Image Simulator Based on Active Sonar Model in Underwater Environment, 2018 15*th International Conference on Ubiquitous Robots* (*UR*), 2018). From this, a virtual sonar response is generated (e.g., acoustic echo responses resolved by echo runtimes and frequencies, optionally preprocessed analogously to operation 102). The necessary elastic tissue parameters of lung tissue, bronchial walls etc. are varied over a reasonable range in order to achieve a large training data set (see, e.g., Jau-Yi Wang, Patrick Mesquida, Prathap Pallai, Chris J Corrigan, Tak H Lee, Dynamic Properties of Human Bronchial Airway Tissues, 2011, https://arxiv.org/abs/1111.5645; Andrikakou, P., Vickraman, K. & Arora, H. On the behaviour of lung tissue under tension and compression. Nature, Sci Rep 6, 36642 (2016). https://doi.org/10.1038/srep36642).

The training images 37 are labeled with lung disease or injury categories of the historical patients. Audio signals for the training images 37 can then be simulated to generate simulated audio signals labeled with lung disease or injury categories. The model 38 can then be trained using the simulated audio signals labeled with lung disease or injury categories.

In another embodiment, the audio signal 31 comprises multiple audio signals 31 acquired over a time frame, and the mapping operation 104 includes mapping the resonant frequencies 36 of the audio signal 31 over the time frame to the one or more lung disease or injury condition categories based at least on an expected progression of at least one lung disease or injury condition over the time frame.

In another embodiment, in addition to the lung disease or injury condition categories, the mapping operation 104 can include mapping the resonant frequencies 36 further to one or more patient categories (e.g., (lung volume classes, airway caliber classes, or other patient-specific characteristics of the patient's lungs/airway). To do so, the resonant frequencies 36 are input to the ML model 38, and the ML model 38 is used to generate one or more mechanical ventilation estimates for the mechanical ventilator 2.

In another approach for generating the labeled training data for training the ML model 38, audio signals can be measured using instances of the acoustic coupler 30, 32 from historical patients with known lung disease or injury condition categories, and optionally also for patients of different patient categories.

While the illustrative embodiment of FIG. 2 uses the trained mapping ML model 38 to map the audio signal to one or more lung disease or injury condition categories, other approaches can be used. For example, first principles analysis of the (optionally preprocessed) audio signal 31 can be used. As a specific example, buildup of mucus in the lungs can lower the peak values of the resonant frequencies 36, so that low peak height values can be mapped to mucus buildup.

At an optional operation 106, the mapped one or more lung disease or injury condition categories is output, for example on the display device 14 or the loudspeaker 17. Additionally or alternatively, at an operation 108, a recommended adjustment to one or more parameters of the mechanical ventilation therapy delivered to the patient is determined based at least on the mapped lung disease or injury condition categories and displaying the recommended adjustment on the display device 14. For example, if the lung volume as estimated from the sonar response is not consistent with the air volume provided by the mechanical ventilation, then appropriate adjustment is recommended. In another example, if the bronchial airway diameters as estimated from the sonar response are not consistent with the air pressure provided by the mechanical ventilation, then appropriate adjustment is recommended. At an optional operation 110, the electronic controller 13 can control the mechanical ventilator 2 adjust one or more parameters of the mechanical ventilation therapy delivered to the patient in response to apply the recommended adjustment to the mechanical ventilator 2.

Figure 3:
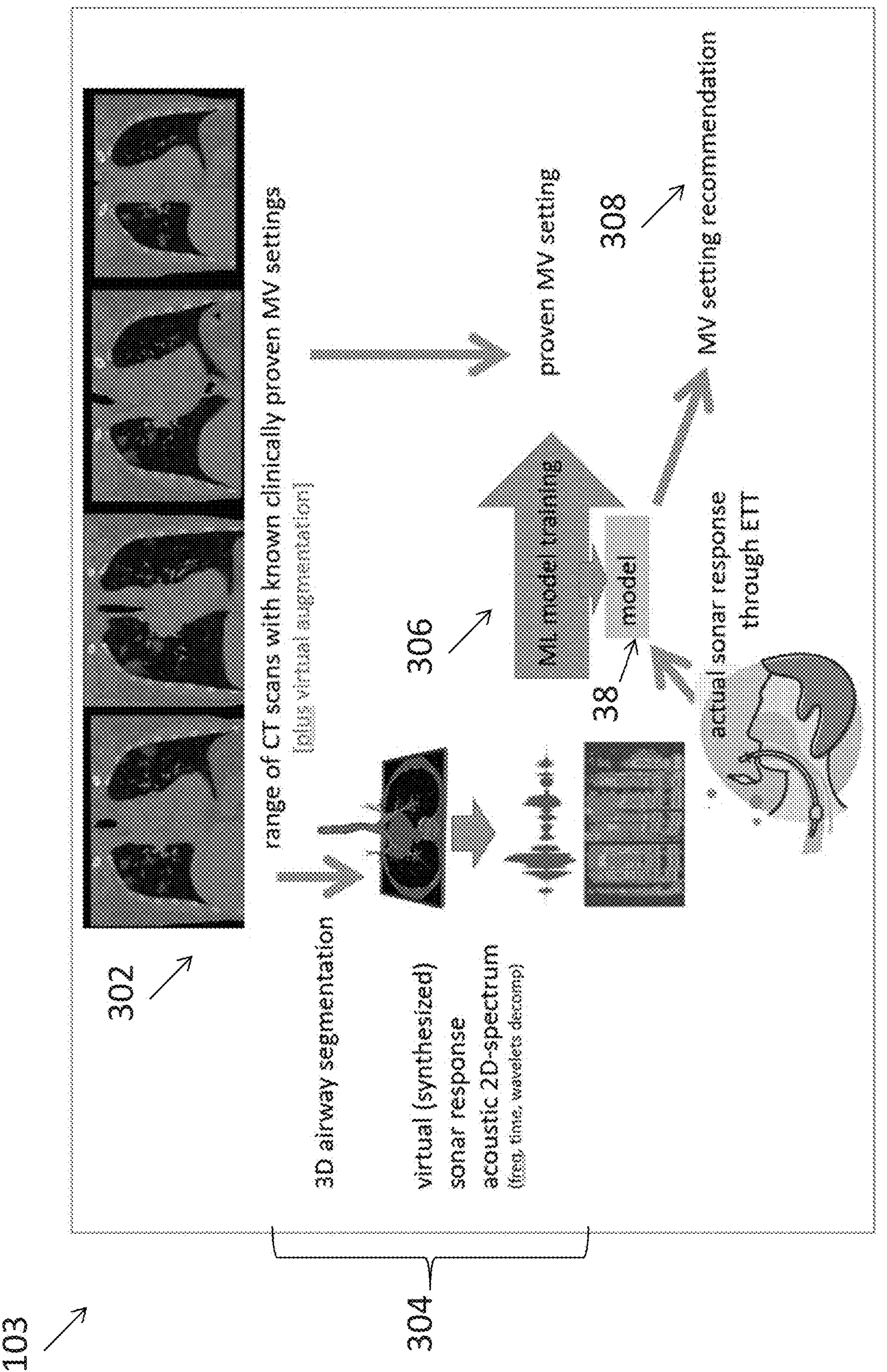
FIG. 3 shows a schematic representation of an operation from FIG. 2.

FIG. 3 shows an example of the training operation 103. At an operation 302, a range of CT scans with known-clinically proven mechanical ventilation settings are obtained. At an operation 304, the CT scans are segmented to produce a virtual sonar response. At an operation 306, the virtual sonar response is used to train the ML model 38. At an operation 308, the trained ML model 38 is used to determine a mechanical ventilation setting recommendation.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A respiration monitoring device comprising an electronic controller configured to:

receive an audio signal that is acoustically coupled with an airway of a patient receiving mechanical ventilation therapy from a mechanical ventilator;

map resonant frequencies extracted from the audio signal to one or more lung disease or injury condition categories; and at least one of:

display the mapped one or more lung disease or injury condition categories on a display device; and determine a recommended adjustment to one or more parameters of the mechanical ventilation therapy delivered to the patient based at least on the mapped lung disease or injury condition categories and displaying the recommended adjustment on the display device;

wherein the electronic controller is configured to map the resonant frequencies to the one or more lung disease or injury condition categories by inputting the resonant frequencies to a resonant frequencies-to-lung disease or injury condition mapping machine-learning (ML) model, wherein the ML model is trained by:

obtaining training images of a plurality of historical patients wherein the training images are labeled with lung disease or injury categories of the historical patients;

simulating audio signals for the training images to generate simulated audio signals labeled with lung disease or injury categories; and training the resonant frequencies-to-lung disease or injury condition mapping ML model using the simulated audio signals labeled with lung disease or injury categories.

2. The device of claim 1, wherein the obtaining of the training images includes:

receiving as-acquired training images of the plurality of historical patients;

segmenting the as-acquired training images to delineate respiratory features including at least the lungs; and modifying the delineated respiratory features in accordance with specific lung disease or injury categories to generate the training images labeled with the specific lung disease or injury categories.

3. The device of claim 1, wherein the training images comprise computed tomography (CT) images.

4. The device of claim 1, wherein the audio signal comprises audio signals acquired over a time frame, and the electronic controller is configured to:

map the resonant frequencies of the audio signal over the time frame to the one or more lung disease or injury condition categories based at least on an expected progression of at least one lung disease or injury condition over the time frame.

5. The device of claim 1, wherein the electronic controller is configured to:

determine a recommended adjustment to one or more parameters of the mechanical ventilation therapy delivered to the patient based on the one or more lung disease or injury condition categories and display the recommended adjustment on the display device.

6. The device of claim 1, wherein the electronic controller is configured to:

preprocess the audio signal to extract the resonant frequencies of the audio signal;

wherein the mapping of the audio signal to the one or more lung disease or injury condition categories comprises mapping the extracted resonant frequencies to the one or more lung disease or injury condition categories.

7. The device of claim 6, wherein the electronic controller is configured to extract the resonant frequencies of the audio signal in a range of 100 Hz-5 kHz.

8. The device of claim 1, further including:

an endotracheal tube (ETT) configured for insertion into a trachea of the patient and operably connected to the mechanical ventilator; and an acoustic coupler configured to be attached to a portion of the ETT not disposed within the trachea, the acoustic coupler configured to generate the audio signal acoustically coupled with the airway of the patient.

9. The device of claim 8, wherein the acoustic coupler comprises:

a microphone configured to acquire the audio signal; and a speaker configured to create the audio signal that is acoustically coupled with the airway of the patient.

10. The device of claim 1, further including:

a mechanical ventilator configured to deliver the mechanical ventilation therapy to the patient.

11. The device of claim 10, wherein the electronic controller is programmed to determine the recommended adjustment and to:

control the mechanical ventilator to apply the recommended adjustment to the mechanical ventilator.

* * * * *